US011872316B2

(12) United States Patent
Funda et al.

(10) Patent No.: US 11,872,316 B2
(45) Date of Patent: *Jan. 16, 2024

(54) DELIVERY SYSTEM

(71) Applicant: DSM IP ASSETS B.V., Heerlen (NL)

(72) Inventors: Elger Funda, Kaiseraugst (CH); Odile Krainz, Kaiseraugst (CH); Robert Steinert, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/761,053

(22) PCT Filed: Oct. 30, 2018

(86) PCT No.: PCT/EP2018/079665
§ 371 (c)(1),
(2) Date: May 1, 2020

(87) PCT Pub. No.: WO2019/086427
PCT Pub. Date: May 9, 2019

(65) Prior Publication Data
US 2021/0177766 A1    Jun. 17, 2021

(30) Foreign Application Priority Data
Nov. 3, 2017  (EP) .................................. 17199806

(51) Int. Cl.
| | | |
|---|---|---|
| *A61K 9/28* | (2006.01) | |
| *A23K 20/174* | (2016.01) | |
| *A23K 40/30* | (2016.01) | |
| *A23P 20/10* | (2016.01) | |
| *A23L 33/15* | (2016.01) | |
| *A61K 31/525* | (2006.01) | |
| *A23P 10/30* | (2016.01) | |
| *A61K 8/11* | (2006.01) | |
| *A61K 8/67* | (2006.01) | |
| *A61K 9/20* | (2006.01) | |
| *A61K 9/48* | (2006.01) | |
| *A61K 9/50* | (2006.01) | |

(52) U.S. Cl.
CPC ............ *A61K 9/286* (2013.01); *A23K 20/174* (2016.05); *A23K 40/30* (2016.05); *A23L 33/15* (2016.08); *A23P 10/30* (2016.08); *A23P 20/105* (2016.08); *A61K 8/11* (2013.01); *A61K 8/673* (2013.01); *A61K 9/2095* (2013.01); *A61K 9/2813* (2013.01); *A61K 9/2886* (2013.01); *A61K 9/4833* (2013.01); *A61K 9/5026* (2013.01); *A61K 9/5036* (2013.01); *A61K 9/5073* (2013.01); *A61K 9/5089* (2013.01); *A61K 31/525* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2013/0115280 A1 | 5/2013 | Moro | |
| 2016/0158174 A1 | 6/2016 | Hayashi et al. | |
| 2016/0220505 A1* | 8/2016 | Temtsin Krayz | .... A61K 9/2018 |

FOREIGN PATENT DOCUMENTS

| | | |
|---|---|---|
| CN | 101287443 | 10/2008 |
| CN | 101677958 | 3/2010 |
| CN | 101896170 | 11/2010 |
| CN | 106572979 | 4/2017 |
| CN | 106998779 | 8/2017 |
| EP | 2914135 | 9/2015 |
| JP | 2017532050 | 11/2017 |

OTHER PUBLICATIONS

International Search Report for PCT/EP2018/079665, dated Jan. 18, 2019, 4 pages.
Written Opinion of the ISA for PCT/EP2018/079665, dated Jan. 18, 2019, 7 pages.
Ghazi Ben Messaoud et al., "Physico-chemical properties of alginate/shellac aqueous-core capsules: Influence of membrane architecture on riboflavin release", Carbohydrate Polymers, Mar. 3, 2016, vol. 144, pp. 428-437.
Mohammad Ali Khosravi Zanjani et al., "Microencapsulation of Probiotics by Calcium Alginate-gelatinized Starch with Chitosan Coating and Evaluation of Survival in Simulated Human Gastrointestinal Condition", Iranian Journal of Pharmaceutical Research, Jan. 1, 2014, vol. 13, No. 3, 10 pages.
Jose, S. et al., "Colon Targeted Drug Delivery: Different Approaches," J. Young Pharm., 2009, vol. 1, No. 1, pp. 13-19.
Notice of Reasons for Rejection for JP Patent Appln No. P2020-518607 dated Mar. 18, 2022 (English-language translation).

* cited by examiner

*Primary Examiner* — Patricia Duffy
*Assistant Examiner* — Garen Gotfredson
(74) *Attorney, Agent, or Firm* — NIXON & VANDERHYE P.C.

(57) ABSTRACT

The present invention relates to a new delivery system for nutritional ingredients (nutraceuticals). These nutritional ingredients are useful for gut and metabolic health in monogastric animals, especially in humans.

10 Claims, No Drawings

DELIVERY SYSTEM

This application is the U.S. national phase of International Application No. PCT/EP2018/079665 filed 30 Oct. 2018, which designated the U.S. and claims priority to EP Patent Application No. 17199806.5 filed 3 Nov. 2017, the entire contents of each of which are hereby incorporated by reference.

The present invention relates to a new delivery system of nutritional ingredients (nutraceuticals) for the large intestine. These nutritional ingredients are useful for gut and metabolic health in monogastric animals (such as swine and poultry as well as fish), especially in humans.

During the last few year, an increase in consumer interest in products that promote gut health could be observed. Many new products came on the market and where accepted widely by the consumers.

There has also been increased investigation into the potential effects of gut microbiota on metabolism and immunity, as well as obesity, inflammation, cardiovascular disease and diabetes.

Interesting and important compounds in regard to gut health are for example the short chain fatty acids (SOFA).

It is believed that recognition of SCFAs by receptors on intestinal epithelial cells turn on systemic biochemical signals to positively regulate glucose metabolism and direct the expenditure of host energy metabolism away from fat storage. SFCAs are also believed to act as an antimicrobial agent toward select fungi and bacteria at low pH when they are in their dissociated form to advantageously modulate the gut microbiota in favor of beneficial microbes.

Other substances beneficial for gut health of monogastric animals like pigs (swine), fish or poultry and humans are organic acids, omega 3 fatty acids, omega 6 fatty acids, omega 8 fatty acids, long chain fatty acids, polyphenols (such as resveratrol or genistein), prebiotics, probiotics, essential oils, or antimicrobial peptides. Also these substances will often be degraded or absorbed to a large extend before reaching the large intestine.

The main issue of the SOFA is that they should be released in the large intestine, where they are effective.

It can be observed that the SOFA are absorbed before arriving in the large intestine. The efficacy of the SOFA in the large intestine is limited due to absorption in the stomach and small intestine (before being released in the large intestine).

Release in the small or large intestine is usually achieved with controlled release capsules or tablets. The active substances are incorporated in a capsule or tablet that is coated with one or more coatings that lead to controlled release. However, tablets and capsules as delivery system have several drawbacks. The amount of active that can be incorporated in a single tablet or capsule limited by the available volume. Especially very young and elderly patients have difficulties with swallowing tablets or capsules. Residence time of capsules and tablets in the stomach is very variable and release is very punctual, which may lead to very high local concentrations of the active, which may cause detrimental effects.

Multiparticulate forms like powders, granules, beadlets or pellets overcome these drawbacks. However, application of controlled release coatings on multiparticulate dosage forms is difficult due to the larger specific surfaces as compared to tablets or capsules. To achieve an evenly distributed coating layer with sufficient thickness, the required amount of coating material is much higher than for tablets or capsules, reducing the available space for payload.

Suitable coating materials for release in the small intestine often comprise pH sensitive polymers. This approach utilizes the existence of the pH gradient in the GIT that increases progressively from the stomach (pH 1.5-3.5) and small intestine (pH 5.5-6.8) to the large intestine (6.4-7.0). The most commonly used pH-dependent polymers are derivatives of acrylic acid and cellulose. Various pH-dependent coating polymers include cellulose acetate phthalate (CAP) (Aquateric®), poly vinyl acetate phthalate (PVAP) (Coateric®), hydroxypropyl methyl cellulose phthalate (HPMCP), and methacrylic acid copolymers, commonly known as methacrylate copolymers or Eudragit.

An important limitation of the pH sensitive coating technique is the uncertainty of the location and environment in which the coating may start to dissolve. It is possible that enteric coating alone may lead to premature drug release in the small intestine due to a variation in GI motility.

The use of GI microflora as a mechanism of drug release in the colonic region has been of great interest to researchers in the past. The majority of bacteria are present in the distal gut although they are distributed throughout the GI tract. The colonic bacteria are predominately anaerobic in nature and secrete enzymes that are capable of metabolizing both endogenous and exogenous substrates such as carbohydrates and proteins that escape digestion in the upper GI tract. Polysaccharides naturally occurring in plant (e.g., pectin, guar gum, inulin), animal (e.g., chitosan, chondroitin sulfate), algal (e.g., alginates), or microbial (e.g., dextran) origins were studied for colon targeting. These are broken down by the colonic microflora to simple saccharides by saccharolytic species like bacteroides and bifidobacteria. [Jose, S., K. Dhanya, T. A. Cinu, J. Litty and A. J. Chacko (2009). "Colon targeted drug delivery: different approaches." J. Young Pharm. 1(1): 13-19.].

Although specifically degraded in the large intestine, many of these polymers are hydrophilic in nature, and swell under exposure to upper GI conditions, which leads to premature drug release. Moreover, these fermentable usually show very high viscosity in solution, which makes them difficult or impossible to process in higher concentration.

Fermentable biopolymers have been used as encapsulating matrix. In matrix encapsulation, the active substance is homogenously distributed in a protective matrix, in this case a fermentable biopolymer. However, matrix encapsulation has several serious drawbacks. Due to the high viscosity of the biopolymers, the matrix solution, e.g. in a spray drying or gel encapsulation is very dilute, making it difficult and expensive to dry. Payload in matrix encapsulation is relatively low (typically less than 50%).

Now the goal of the present invention was to find an improved multiparticulate delivery system (formulation) to improve the stability of nutraceuticals (such as organic acids, omega 3 fatty acids, omega 6 fatty acids, omega 8 fatty acids, long chain fatty acids, polyphenols (such as resveratrol or genistein), prebiotics, probiotics, essential oils, or antimicrobial peptides) during the transport through the stomach and the small intestine (before being released in the large intestine) so that the availability and the efficacy of the nutraceuticals are improved.

Furthermore, the new delivery system should be producible in a simple and industrial applicable way.

It was found that when a solid core comprising at least one nutraceutical is coated with a specific inner and a specific outer coating, then the delivery system has improved properties. Furthermore, the delivery system can be produced in bath-wise as well as in by continuous process.

The new delivery system (DS) according to the present invention consists of
(a) a solid core, which comprises at least one nutraceutical, and
(b) an inner coating comprising at least one fermentable biopolymer, which is crosslinked, and
(c) an outer coating which is resistant to stomach conditions and releasing in the small intestine.

The active substance, which is in the solid core is a nutraceutical.

In the context of the present invention nutraceuticals are compounds that provide health benefits in the animal.

Preferred nutraceuticals in the present invention are organic acids, omega 3 fatty acids, omega 6 fatty acids, omega 8 fatty acids, long chain fatty acids, polyphenols (such as resveratrol or genistein), prebiotics, probiotics, essential oils, and antimicrobial peptides.

The solid core (and also the delivery system) according to the present invention does not comprise any vitamin B (especially vitamin B2). This means that the solid core (and the delivery system) is free of any vitamin B (especially vitamin B2)

Therefore, the present invention relates to a delivery system (DS1), which is the delivery system (DS), wherein the at least one nutraceutical is chosen from the group consisting of organic acids, omega 3 fatty acids, omega 6 fatty acids, omega 8 fatty acids, long chain fatty acids, polyphenols (such as resveratrol or genistein), prebiotics, probiotics, essential oils, and antimicrobial peptides.

Therefore, the present invention relates to a delivery system (DS1'), which is the delivery system (DS) or (DS1), wherein the solid core (and also the coatings) does not comprise any vitamin B (especially vitamin B2). (This means that the present invention relates to a delivery system (DS1'), which is the delivery system (DS) or (DS1), wherein the solid core (and also the coatings) is free of any vitamin B (especially vitamin B2)).

Preferred organic acids are short chain fatty acids (SCFAs) as well as their salts. Short-chain fatty acids are fatty acids with two to six carbon atoms. In the context of the present invention SCFAs are the following: formic acid, acetic acid, propionic acid, butyric acid, isobutyric acid, valeric acid, and isovaleric acid and salts of these acids. Especially preferred is propionic acid and salts thereof.

Therefore, the present invention relates to a delivery system (DS2), which is the delivery system (DS), (DS1) or (DS1'), wherein the at least one nutraceutical is chosen from the group consisting of organic acids (and salts thereof), prebiotics, probiotics, essential oils, and antimicrobial peptides.

Therefore, the present invention relates to a delivery system (DS3), which is the delivery system (DS), (DS1) or (DS1'), wherein the at least one nutraceutical is chosen from the group of organic acids (and salts thereof).

Therefore, the present invention relates to a delivery system (DS3'), which is the delivery system (DS3), wherein the nutraceutical is propionic acid (and/or salts thereof).

Therefore, the present invention relates to a delivery system (DS3"), which is the delivery system (DS3), wherein the nutraceutical is butyric acid (and/or salts thereof).

The delivery system according to the present invention comprises an inner coating, which needs to fulfill the criteria as defined. Suitable materials for the inner coating (fermentable biopolymer) are for example alginate, chitosan, pectin, cyclodextrin as well as other gums. Preferred coating materials for the inner coating are alginate or pectin.

The inner coating is crosslinked. This can be done by commonly known crosslinking compounds. In case alginate is used that can be done by Mg and/or Ca ion (by the use of a salt). The crosslinker can be spray onto to core after having applied the inner coating or simultaneously. Or the coated particles can be dipped into a solution comprising the crosslinker.

Preferably the crosslinker is sprayed onto the particles after having applies the inner coating layer.

Another advantage of the present invention also lies therein that the production of the new delivery system according to the present invention can be done batch-wise as well as continuously. In contrast to the systems known from the prior art this is a huge advantage also in view of the industrial production of such product. The details of the process are disclosed below.

Therefore, the present invention relates to a delivery system (DS4), which is the delivery system (DS), (DS1), (DS1') (DS2), (DS3), (DS3') or (DS3"), wherein the material of the inner coating is chosen from group consisting of alginate, chitosan, pectin, cyclodextrin as well as other gums.

Therefore, the present invention relates to a delivery system (DS4'), which is the delivery system (DS4), wherein the material of the inner coating is alginate or pectin.

The inner coating layer is covering the solid core (more or less) completely. Ideally the (layer of the inner coating has (more or less) the same thickness when applied on the solid core.

Usually the thickness of the inner coating layer is at least 5 μm and not more than 20 μm. Preferably, the thickness of the inner coating layer is between 5 μm-10 μm.

Therefore, the present invention relates to a delivery system (DS5), which is the delivery system (DS), (DS1), (DS1') (DS2), (DS3), (DS3'), (DS3"), (DS4) or (DS4'), wherein the thickness of the inner coating layer is 5 μm-10 μm.

The inner coating layer is crosslinked with at least one crosslinking agent. Any suitable crosslinker can be used. Very suitable (and therefore preferred are Mg and Ca ions (they are added in form of a salt).

Therefore, the present invention relates to a delivery system (DS6), which is the delivery system (DS), (DS1), (DS1') (DS2), (DS3), (DS3'), (DS3"), (DS4), (DS4') or (DS5), wherein the inner coating layer is crosslinked with at least one crosslinking agent (preferably with Mg and/or Ca ions).

Therefore, the present invention relates to a delivery system (DS7), which is the delivery system (DS), (DS1), (DS1') (DS2), (DS3), (DS3'), (DS3"), (DS4), (DS4'), (DS5) or (DS6), wherein the crosslinked inner coating layer is Na alginate or Na pectin.

The delivery system according to the present invention comprises an outer coating, which needs to fulfill the criteria as defined. Suitable materials which fulfill the criteria for the outer coating is for example shellac, methacrylate copolymers and fats.

Therefore, the present invention relates to a delivery system (DS8), which is the delivery system (DS), (DS1), (DS1') (DS2), (DS3), (DS3'), (DS3"), (DS4), (DS4'), (DS5); (DS6) or (DS7), wherein the material of the outer coating is chosen from group consisting of shellac, methacrylate copolymers and fats.

The outer coating layer is covering the inner coating (more or less) completely. Ideally the layer of the outer coating has (more or less) the same thickness when applied on the inner coating.

Usually the thickness of the outer layer is at least 10 μm and usually less than 30 μm. Preferably, the thickness of the outer coating layer is between 10 and 20 μm.

Therefore, the present invention relates to a delivery system (DS9), which is the delivery system (DS), (DS1), (DS1') (DS2), (DS3), (DS3'), (DS3"), (DS4), (DS4'), (DS5); (DS6), (DS7) or (DS8), wherein the thickness of the outer coating layer is 10 μm-20 μm.

The solid core of the delivery system according to the present invention is usually 10-85 wt-%, preferably 50-75 wt-%, based on the total weight of the delivery system.

Therefore, the present invention relates to a delivery system (DS10), which is the delivery system (DS), (DS1), (DS1') (DS2), (DS3), (DS3'), (DS3"), (DS4), (DS4'), (DS5); (DS6), (DS7), (DS8) or (DS9), wherein the solid core of the delivery system is 10-85 wt-%, preferably 50-75 wt-%, based on the total weight of the delivery system.

The inner coating of the delivery system according to the present invention is usually 1-20 wt-%, preferably 1-10 wt-%, based on the total weight of the delivery system.

Therefore, the present invention relates to a delivery system (DS11), which is the delivery system (DS), (DS1), (DS1') (DS2), (DS3), (DS3'), (DS3"), (DS4), (DS4'), (DS5); (DS6), (DS7), (DS8), (DS9) or (DS10), wherein the inner coating of the delivery system is 1-20 wt-%, preferably 1-10 wt-%, based on the total weight of the delivery system.

The outer coating of the delivery system according to the present invention is usually 1-30 wt-%, preferably 15-30 wt-%, based on the total weight of the delivery system.

Therefore, the present invention relates to a delivery system (DS12), which is the delivery system (DS), (DS1), (DS1') (DS2), (DS3), (DS3'), (DS3"), (DS4), (DS4'), (DS5); (DS6), (DS7), (DS8), (DS9), (DS10) or (DS11), wherein the outer coating of the delivery system is 1-30 wt-%, preferably 15-30 wt-%, based on the total weight of the delivery system The solid delivery system according to the present invention can be up to 2 mm in size. The size is defined by the longest diameter of the particle. The shape of the particle is not an essential feature of the present invention. Also the size distribution of the particles is no essential. The size and the shape of the particle is mainly defined by the solid core of the delivery system. Depending on the use of the delivery system the size can be adjusted.

The delivery system according to the present invention is produced by commonly known technology.

Usually the solid core is produced in a first step and then the inner and outer coatings are applied.

As disclosed above one of the major advantage of the new delivery system (besides the property of the delivery system) lies in the process of production of the delivery system. The new delivery system can be produced batch-wise of continuously.

When produced batch-wise the new particles can be produce as follows:

In first step the solid core is produced by spray drying process, then in a second step the solid cores (obtained in the first step) are coated by spray coating with the coating material of the inner coating, and then the crosslinker is spray onto the particle. In a third step the outer coating is spray onto the particle obtained by the previous steps and finally the particles are dried.

The advantage of the process is that the steps can be carried in the same apparatus (spray coater) which reduces the technical effort. Nevertheless, it is also possible to i.e. produce the solid cores first, store them and then coat them.

Another option how to produce the new delivery system is a continuous process, wherein the solid cores are produced first and then the coating steps are done spray onto the particle one after the other. These processes are ideal to apply in an industrial scale.

Therefore the present invention also related to a process of production (P) of any of the particles (DS), (DS1), (DS1') (DS2), (DS3), (DS3'), (DS3"), (DS4), (DS4'), (DS5); (DS6), (DS7), (DS8), (DS9), (DS10), (DS11) or (DS12), wherein the process is carried out batchwise.

Therefore the present invention also related to a process of production (P1) of any of the particles (DS), (DS1), (DS1') (DS2), (DS3), (DS3'), (DS3"), (DS4), (DS4'), (DS5); (DS6), (DS7), (DS8), (DS9), (DS10), (DS11) or (DS12), wherein the process is carried out continuously.

The new delivery systems (DS), (DS1), (DS1') (DS2), (DS3), (DS3'), (DS3"), (DS4), (DS4'), (DS5); (DS6), (DS7), (DS8), (DS9), (DS10), (DS11) and/or (DS12) according to the present invention can be used as such or incorporated into any application forms.

The new delivery systems (DS), (DS1), (DS1') (DS2), (DS3), (DS3'), (DS3"), (DS4), (DS4'), (DS5); (DS6), (DS7), (DS8), (DS9), (DS10), (DS11) and/or (DS12) can used as such in any dietary supplement, food product, feed product, personal care product or pharmaceutical product.

The new delivery systems ((DS), (DS1), (DS1') (DS2), (DS3), (DS3'), (DS3"), (DS4), (DS4'), (DS5); (DS6), (DS7), (DS8), (DS9), (DS10), (DS11) and/or (DS12) can also be part of a premix formulation, which can then be used to formulate any dietary supplement, food product, feed product, personal care product or pharmaceutical product.

The invention also relates to a process for the production of a premix, dietary supplement, food product, feed product, personal care product or pharmaceutical product using at least one delivery system (DS), (DS1), (DS1') (DS2), (DS3), (DS3'), (DS3"), (DS4), (DS4'), (DS5); (DS6), (DS7), (DS8), (DS9), (DS10), (DS11) or (DS12).

The invention also relates to a premix, dietary supplement, food product, feed product, personal care product or pharmaceutical product comprising at least one delivery system (DS), (DS1), (DS1') (DS2), (DS3), (DS3'), (DS3"), (DS4), (DS4'), (DS5); (DS6), (DS7), (DS8), (DS9), (DS10), (DS11) or (DS12).

The following examples serve to illustrate specific embodiments of the invention claimed herein. All percentages are given in relation to the weight and all the temperatures are given in degree Celsius.

EXAMPLES

Example 1

30 g Na alginate (grinsted sodium alginate) are dissolved in 1500 g water at 50° C. with stirring. 3.2 g Ca chloride dihydrate is dissolved in 407 g water. 200 g Ca Propionate (Sigma-Aldrich) is filled in a fluid-bed processor (WFP mini, DMR, Wurster configuration). All coating steps were performed at a product temperature of about 40° C. The alginate solution is sprayed on the fluidized Ca propionate powder first. After spraying of the alginate solution, the feeding tube is briefly rinsed with water. The Ca chloride solution is sprayed on the inner coating at 40° C. for hardening. After the hardening solution, 400 g aqueos shellac preparation with a solids content of 25% (Marcoat 125N) is sprayed as outer coating. After spraying of the shellac, the product is dried in the fluid bed. 324 g coated granules were obtained.

Composition of the final coated granulate was 60% Ca-propionate, 9% alginate, 1% Ca chloride and 30% shellac.

Protection of propionate under stomach conditions was tested with 0.1N HCl at 37.5° C. using a USP-1 (SOTAX) apparatus. After 2 hours only 12% of the propionate was released.

Example 2: Comparative Example without Hardening the Inner Layer

Ca-propionate was coated similar to example 1, skipping the hardening step (spraying of Ca chloride). Composition of the final coated granulate was 58% Ca-propionate, 7% Na alginate and 35% shellac.

Protection of propionate under stomach conditions was tested with 0.1N HCl at 37.5° C. using a USP-1 (SOTAX) apparatus. After 2 hours 58% of the propionate was released.

The invention claimed is:

1. A particulate delivery system comprising coated particles adapted to deliver at least one nutraceutical to large intestines of a patient, wherein each of the coated particles consists of:
   (a) 10-85 wt. %, based on total weight of the delivery system, of a particulate solid core consisting of butyric acid and/or salts thereof as a nutraceutical,
   (b) 1-20 wt. %, based on total weight of the delivery system, of an inner coating having a substantially uniform thickness of 5 μm to 20 μm which covers the solid core, wherein the inner coating comprises at least one fermentable crosslinked biopolymer, and
   (c) 1-30 wt. %, based on total weight of the delivery system, of an outer coating having a substantially uniform thickness of 10 μm to 30 μm which covers the inner coating, wherein the outer coating is formed of a material resistant to stomach and small intestine conditions to thereby allow release of the at least one nutraceutical in the large intestines of the patient.

2. The particulate delivery system according to claim 1, wherein the at least one fermentable crosslinked biopolymer of the inner coating is selected from the group consisting of alginate, chitosan, pectin, cyclodextrin and gums.

3. The particulate delivery system according to claim 1, wherein the inner coating layer is crosslinked with Mg and/or Ca ions.

4. The particulate delivery system according to claim 1, wherein the outer coating is formed of a material selected from the group consisting of shellac, methacrylate copolymers and fats.

5. The particulate delivery system according to claim 1, wherein the inner coating has a substantially uniform thickness of 5 μm to 10 μm.

6. The particulate delivery system according to claim 1, wherein the outer coating has a substantially uniform thickness of 10 μm to 20 μm.

7. A process for producing the particulate delivery system according to claim 1, wherein the process comprises forming the coated particles by the sequential steps of:
   (a) producing the particulate solid core by a spray drying process;
   (b) spraying at least one fermentable uncrosslinked biopolymer onto the particulate solid core;
   (c) contacting the at least one fermentable uncrosslinked biopolymer with a crosslinker to form the inner coating which covers the solid core comprised of the at least one crosslinked biopolymer;
   (d) spraying the material resistant to stomach and small intestine conditions onto the inner coating to thereby form the outer coating of the particulate delivery system; and thereafter
   (e) drying the coated particles.

8. The process according to claim 7, wherein the steps (a)-(e) of the process are carried out batch-wise or continuously.

9. A product which comprises the particulate delivery system according to claim 1.

10. The product according to claim 9, wherein the product is a premix product, a dietary supplement product, a food product, a feed product, a personal care product or a pharmaceutical product.

* * * * *